April 30, 1957
H. I. BURKEY
Plant Pat. 1,597
SNAPDRAGON PLANT
Filed Aug. 22, 1956
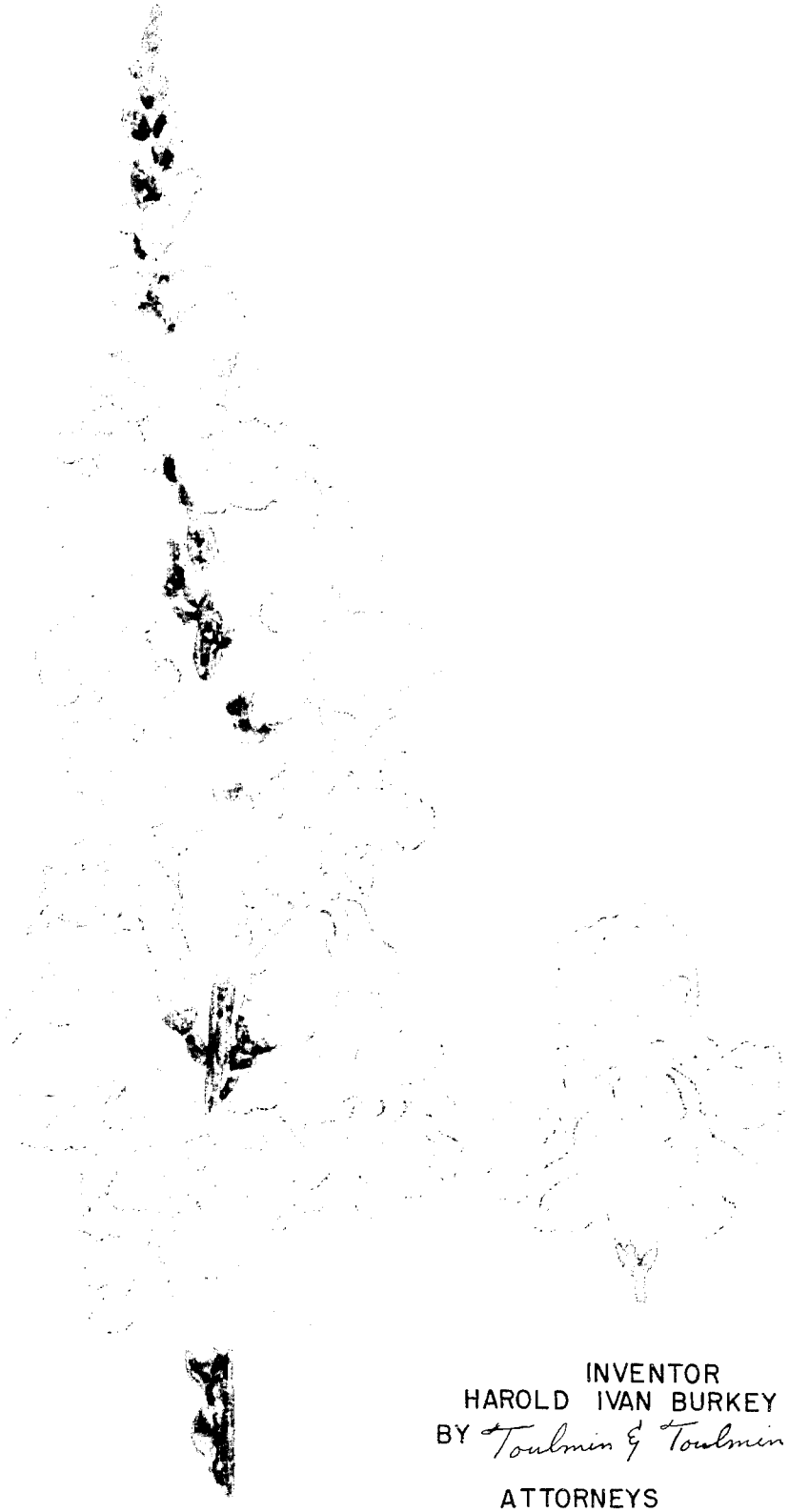
INVENTOR
HAROLD IVAN BURKEY
BY Toulmin & Toulmin
ATTORNEYS United States Patent Office Plant Pat. 1,597
Patented Apr. 30, 1957

1,597

SNAPDRAGON PLANT

Harold Ivan Burkey, Stuart, Fla.

Application August 22, 1956, Serial No. 605,682

1 Claim. (Cl. 47—60)

My present discovery relates to a new and distinct variety of snapdragon (Antirrhinum) plant which is a mutational variety from the variety of snapdragon plant shown and described in my Plant Patent No. 1,270, of April 20, 1954.

This new snapdragon plant is distinguishable from the parent plant mainly in the color of its blossoms. The flowers are of a distinctly light pink coloration overall, having splashes of a deeper pink.

This new variety has been asexually reproduced by cuttings in my greenhouses and farm in Stuart, Florida, and has remained true to type and the herein described characteristics through the propagation of over 500 plants during the period of six months. There are presently 500 plants in existence at my farm in Stuart, Florida. No seeds have been produced by this new variety so all propagation must be asexual.

Like the parent plant this new variety of snapdragon shows a pronounced reduplication of its petal-like parts and is sharply distinguished from other double snapdragon by the profusion of blossoms; the absence of excessive lateral shoots; the variety is vigorous and easy to propagate, has a hard stiff stem and exhibits a fragrance.

The accompanying illustrations show in full color a view embodying the invention and a smaller front view of the flower of the new variety.

Referring to the illustrations the upper petal lobes, which are integral with the corolla tube, are oppositely disposed, two in number, curl backwardly, are of substantially equal size and have their center edges overlapping; the lower petal lobes are three in number, curl backwardly to partially cover the corolla tube, are crinkled on the edges and overlap each other slightly.

True functional stamens are not present but the usual six to eight stamens bear at their upper ends small pink wrinkled petals; approximately one-half of these stamens, usually those on the lower lobes, have yellow markings which extend up to the pink of the small petals and set off the distinctive pink coloration of the petals.

The plant has a hard, stiff stem, and the length of the stem and of the spike vary with conditions such as weather and age; at maturity the stem may have a considerable height, a length of six feet not being unusual, as in the parent plant. The leaves are arranged irregularly alternately around the stem; the flowers are closely grouped and present a compact appearance.

The upper end of the spike has a plurality of flower buds with accompanying bracts and these progressively open as the variety ages. In the embodiment of the invention illustrated the spikes are somewhat short as the illustration was made at a time somewhat before full growth had been attained.

As shown in the drawings, and particularly in the smaller figure, the corolla tube which carries the petal lobes has in the lower portion a pink tint similar to that found in the petal, which tint is emphasized if, as occasionally happens, a number of the corolla tubes are in close visible proximity.

The pink of the corolla tube is tinted with a greenish hue which emerges into the distinctive and characteristic light pink of the petals. The petals themselves are slightly darker in the center than in the body and give to the variety the distinctive pink coloration. The yellow nonfunctional stamens protrude centrally of the flower and enhance the overall appearance.

The color designations of the variety, according to "A Dictionary of Color" by Maerz and Paul, are as follows:

| | Plate | Letter | Number |
|---|---|---|---|
| Main flower color-lobes | 2 | D | 2 |
| Splashes of dark pink within the boundaries of the light pink | 2 | D | 4 |
| Edge coloration-lobes | 35 | J | 7 |
| Petals | 2 | D | 3 |
| Stamen markings | 9 | J | 1 |
| Corolla tube | 2 | D | 2 |
| Streaks of green on the corolla tube | 12 | G | 1 |
| Stem | 21 | G | 10 |
| Sepals | 21 | K | 10 |
| Leaves | 21 | G | 10 |

Having thus disclosed my discovery, I claim:

A new and distinct variety of double snapdragon plant characterized particularly by its pleasing, distinctive characteristic pink coloration of the flowers, having splashes of deep pink on a background of light pink; the compactness of the flowers; the absence of excessive lateral shoots; and its vigor and hard stiff stems.

No references cited.